United States Patent
Ross et al.

(10) Patent No.: US 10,064,611 B2
(45) Date of Patent: Sep. 4, 2018

(54) METHODS AND DEVICES FOR VEIN HARVESTING

(71) Applicant: COVIDIEN LP, Mansfield, MA (US)

(72) Inventors: Anthony B. Ross, Boulder, CO (US); Ashish Sharma, Boulder, CO (US); Eric R. Larson, Boulder, CO (US); William H. Nau, Jr., Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 448 days.

(21) Appl. No.: 14/805,940

(22) Filed: Jul. 22, 2015

(65) Prior Publication Data

US 2017/0020494 A1    Jan. 26, 2017

(51) Int. Cl.
| | |
|---|---|
| A61B 1/32 | (2006.01) |
| A61B 17/00 | (2006.01) |
| A61B 17/02 | (2006.01) |
| A61B 18/14 | (2006.01) |
| A61B 17/32 | (2006.01) |
| A61B 18/00 | (2006.01) |

(52) U.S. Cl.
CPC .... *A61B 17/00008* (2013.01); *A61B 17/0218* (2013.01); *A61B 18/1482* (2013.01); *A61B 2017/00398* (2013.01); *A61B 2017/00477* (2013.01); *A61B 2017/320052* (2013.01); *A61B 2017/320056* (2013.01); *A61B 2018/0063* (2013.01); *A61B 2018/00601* (2013.01)

(58) Field of Classification Search
CPC combination set(s) only.
See application file for complete search history.

(56) References Cited

U.S. PATENT DOCUMENTS

| | | |
|---|---|---|
| 2,011,169 A | 8/1935 | Wappler |
| 2,028,635 A | 1/1936 | Wappler |
| 3,659,606 A | 5/1972 | Reimels |
| 3,764,427 A | 10/1973 | Reimels |
| 3,788,325 A | 1/1974 | Jacobsen |
| 4,052,980 A | 10/1977 | Grams et al. |
| 4,528,982 A | 7/1985 | Wellenstam |
| 4,655,217 A | 4/1987 | Reed |
| 5,011,489 A | 4/1991 | Salem |
| 5,013,312 A | 5/1991 | Parins et al. |
| 5,373,840 A | 12/1994 | Knighton |
| 5,395,384 A | 3/1995 | Duthoit et al. |
| 5,522,827 A | 6/1996 | Combs et al. |
| 5,571,172 A | 11/1996 | Chin |
| 5,591,183 A | 1/1997 | Chin |
| 5,593,418 A | 1/1997 | Mollenauer |
| 5,601,581 A | 2/1997 | Fogarty et al. |
| 5,601,589 A | 2/1997 | Fogarty et al. |
| 5,607,441 A | 3/1997 | Sierocuk et al. |
| 5,653,722 A | 8/1997 | Kieturakis |
| 5,658,282 A | 8/1997 | Daw et al. |
| 5,667,480 A | 9/1997 | Knight et al. |
| 5,676,636 A | 10/1997 | Chin |
| 5,690,668 A | 11/1997 | Fogarty et al. |
| 5,695,514 A | 12/1997 | Chin |

(Continued)

FOREIGN PATENT DOCUMENTS

| | | |
|---|---|---|
| DE | 19906260 A1 | 9/1999 |
| WO | 03000139 A1 | 1/2003 |

(Continued)

OTHER PUBLICATIONS

Extended European Search Report for EP 16180494 dated Dec. 23, 2016.

(Continued)

*Primary Examiner* — Sameh Boles

(57) ABSTRACT

A vein harvesting device. The vein harvesting device includes a retractor and a drive shaft. The retractor includes an elongated portion defining a longitudinal axis, and supports a first engagement structure including a plurality of first tines. The drive shaft includes an elongated portion, and is movable along the longitudinal axis with respect to the retractor such that the elongated portion of the drive shaft contacts the first engagement structure causing the plurality of first tines to move about the longitudinal axis from a first position to a second position.

20 Claims, 6 Drawing Sheets

(56) References Cited

U.S. PATENT DOCUMENTS

| | | |
|---|---|---|
| 5,702,417 A | 12/1997 | Hermann |
| 5,707,382 A | 1/1998 | Sierocuk et al. |
| 5,716,325 A | 2/1998 | Bonutti |
| 5,722,934 A | 3/1998 | Knight et al. |
| 5,725,479 A | 3/1998 | Knight et al. |
| 5,730,748 A | 3/1998 | Fogarty et al. |
| 5,738,628 A | 4/1998 | Sierocuk et al. |
| 5,759,150 A | 6/1998 | Konou et al. |
| 5,762,604 A | 6/1998 | Kieturakis |
| 5,772,576 A | 6/1998 | Knighton et al. |
| 5,782,753 A | 7/1998 | DeFonzo et al. |
| 5,782,854 A | 7/1998 | Hermann |
| 5,797,946 A | 8/1998 | Chin |
| 5,797,947 A | 8/1998 | Mollenauer |
| 5,800,540 A | 9/1998 | Chin |
| 5,803,903 A | 9/1998 | Athas et al. |
| 5,814,059 A | 9/1998 | Hart et al. |
| 5,814,060 A | 9/1998 | Fogarty et al. |
| 5,817,013 A | 10/1998 | Ginn et al. |
| 5,823,946 A | 10/1998 | Chin |
| 5,827,318 A | 10/1998 | Bonutti |
| 5,836,945 A | 11/1998 | Perkins |
| D403,066 S | 12/1998 | DeFonzo |
| 5,843,104 A | 12/1998 | Samuels |
| 5,853,417 A | 12/1998 | Fogarty et al. |
| RE36,043 E | 1/1999 | Knighton |
| 5,871,496 A | 2/1999 | Ginn et al. |
| 5,873,889 A | 2/1999 | Chin |
| 5,876,413 A | 3/1999 | Fogarty et al. |
| 5,891,140 A | 4/1999 | Ginn et al. |
| 5,893,858 A | 4/1999 | Spitz |
| 5,893,866 A | 4/1999 | Hermann et al. |
| 5,895,353 A | 4/1999 | Lunsford et al. |
| 5,899,912 A | 5/1999 | Eaves, III |
| 5,899,913 A | 5/1999 | Fogarty et al. |
| 5,902,315 A | 5/1999 | DuBois |
| 5,902,316 A | 5/1999 | Mollenauer |
| 5,913,818 A | 6/1999 | Co et al. |
| 5,913,866 A | 6/1999 | Ginn et al. |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,138 A | 7/1999 | Knight et al. |
| 5,938,680 A | 8/1999 | Ginn |
| 5,944,734 A | 8/1999 | Hermann et al. |
| 5,951,584 A | 9/1999 | Hermann |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,979,452 A | 11/1999 | Fogarty et al. |
| 5,980,549 A | 11/1999 | Chin |
| 5,984,937 A | 11/1999 | Morse et al. |
| 5,993,384 A | 11/1999 | Lunsford et al. |
| 5,993,472 A | 11/1999 | Hermann et al. |
| 6,004,340 A | 12/1999 | Hermann et al. |
| 6,013,090 A | 1/2000 | Fogarty et al. |
| 6,019,771 A | 2/2000 | Bennett et al. |
| 6,022,313 A | 2/2000 | Ginn et al. |
| 6,030,396 A | 2/2000 | Samuels |
| 6,030,406 A | 2/2000 | Davis et al. |
| 6,036,713 A | 3/2000 | Kieturakis |
| 6,036,714 A | 3/2000 | Chin |
| 6,042,538 A | 3/2000 | Puskas |
| 6,051,013 A | 4/2000 | Mollenauer |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,080,102 A | 6/2000 | Konou et al. |
| 6,110,170 A | 8/2000 | Taylor et al. |
| 6,129,661 A | 10/2000 | Iafrati et al. |
| 6,139,489 A | 10/2000 | Wampler et al. |
| 6,143,008 A | 11/2000 | Eaves, III |
| 6,162,173 A | 12/2000 | Chin et al. |
| 6,174,313 B1 | 1/2001 | Bonutti |
| 6,193,651 B1 | 2/2001 | DeFonzo |
| 6,193,653 B1 | 2/2001 | Evans et al. |
| 6,196,968 B1 | 3/2001 | Rydin et al. |
| 6,203,557 B1 | 3/2001 | Chin |
| 6,203,559 B1 | 3/2001 | Davis et al. |
| 6,206,823 B1 | 3/2001 | Kolata et al. |
| 6,206,899 B1 | 3/2001 | Ginn |
| 6,228,024 B1 | 5/2001 | Co et al. |
| 6,240,924 B1 | 6/2001 | Fogarty et al. |
| 6,264,670 B1 | 7/2001 | Chin |
| 6,277,137 B1 | 8/2001 | Chin |
| 6,283,963 B1 | 9/2001 | Regula |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,375,665 B1 | 4/2002 | Nash et al. |
| 6,413,208 B1 | 7/2002 | Schollhorn et al. |
| 6,428,468 B1 | 8/2002 | Knighton et al. |
| 6,428,556 B1 | 8/2002 | Chin |
| 6,432,044 B1 | 8/2002 | Lunsford et al. |
| 6,436,116 B1 | 8/2002 | Spitz et al. |
| 6,436,118 B1 | 8/2002 | Kayan |
| 6,443,159 B1 | 9/2002 | Fogarty et al. |
| 6,443,970 B1 | 9/2002 | Schulze et al. |
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,454,784 B1 | 9/2002 | Mollenauer |
| 6,468,206 B1 | 10/2002 | Hipps et al. |
| 6,482,153 B1 | 11/2002 | Hipps et al. |
| 6,506,200 B1 | 1/2003 | Chin |
| 6,511,494 B1 | 1/2003 | Knighton et al. |
| 6,527,771 B1 | 3/2003 | Weadock et al. |
| 6,527,787 B1 | 3/2003 | Fogarty et al. |
| 6,551,335 B1 | 4/2003 | Bardeau et al. |
| 6,572,615 B2 | 6/2003 | Schulze et al. |
| 6,592,582 B2 | 7/2003 | Hess et al. |
| 6,592,604 B2 | 7/2003 | Hess et al. |
| 6,596,010 B1 | 7/2003 | Hermann et al. |
| 6,607,547 B1 | 8/2003 | Chin |
| 6,616,661 B2 | 9/2003 | Wellman et al. |
| 6,623,482 B2 | 9/2003 | Pendekanti et al. |
| 6,648,815 B2 | 11/2003 | Schoellhorn et al. |
| 6,652,521 B2 | 11/2003 | Schulze |
| 6,656,176 B2 | 12/2003 | Hess et al. |
| 6,660,016 B2 | 12/2003 | Lindsay |
| 7,645,289 B2 | 1/2010 | Bayer |
| 2003/0195544 A1 | 10/2003 | Hess et al. |
| 2005/0096670 A1* | 5/2005 | Wellman .......... A61B 17/00008 606/139 |

FOREIGN PATENT DOCUMENTS

| | | |
|---|---|---|
| WO | 03013365 A1 | 2/2003 |
| WO | 03013367 A2 | 2/2003 |

OTHER PUBLICATIONS

EP Office Action for EP 02744699 dated Apr. 6, 2009.
European Examination Report for Application No. 16 180 494.3 dated Oct. 27, 2017 (4 pages).

* cited by examiner

METHODS AND DEVICES FOR VEIN HARVESTING

BACKGROUND

The present disclosure relates to methods and devices for endoscopic surgery, in particular to methods and devices for endoscopic vein harvesting.

TECHNICAL FIELD

Numerous surgical procedures have been developed to replace veins and arteries that have become blocked by disease. As a result of aging and/or disease, veins and arteries may become blocked by plaque deposits, stenosis, or cholesterol. In some instances, these blockages can be treated with artherectomy, angioplasty or stent placement, and coronary bypass surgery is not required. Coronary bypass surgery is required when these other methods of treatment cannot be used or have failed to clear the blocked vein or artery. In the coronary bypass surgery, a vein is harvested from elsewhere in the body and grafted into place (e.g., between the aorta and the coronary artery) beyond the point of blockage.

The coronary bypass surgery requires a length of vein or artery for the graft. It is preferred to use a vein taken from the patient undergoing the bypass surgery. The patient is a ready source of suitable veins that will not likely be rejected by the body after transplantation and grafting onto the aorta and coronary artery. The saphenous vein in the leg is often the best substitute for small veins or arteries such as the coronary arteries, and it is often the preferred vein for use in coronary bypass surgery. This is because the saphenous vein is typically 3 mm to 5 mm in diameter, about the same size as the coronary arteries. Also, the venous system of the legs is sufficiently redundant so that after removal of the saphenous vein, other veins that remain in the leg are adequate to provide adequate blood flow. The radial artery and the cephalic vein in the arm are alternatives that are sometimes used.

In a typical operation previously required to harvest the saphenous vein, the surgeon cut into the leg to allow access to the saphenous vein and cut the vein from the leg. To expose the vein, the surgeon made a series of incisions from the groin to the knee or the ankle leaving one or more skin bridges along the line of the incisions. (Some surgeons make one continuous incision from the groin to the knee or ankle). Handling of the vein must be kept to a minimum, but the vein must be removed from connective tissue, which requires some force. After exposing the vein, the surgeon grasps it with his or her fingers while stripping off the surrounding tissues with dissecting scissors or other scraping instruments. The surgeon uses his or her fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lay under the skin bridges, the surgeon may need to cut one end of the saphenous vein and pull it under the skin bridge to gently pull the vein out from under the skin bridge until the tributary is sufficiently exposed so that it may be ligated and divided. When the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can also be used to harvest veins for a femoral popliteal bypass, in which an occluded femoral artery is bypassed from above the occlusion to the popliteal artery above or below the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery. The procedures may be used also to harvest veins for femoral-tibial, femora-peroneal, aorto-femoral, and iliac-femoral bypass operations and any other bypass operation.

As can be seen from the description of the harvesting operation, the harvesting operation is very traumatic in its own right. In the case of coronary artery bypass, this operation is carried out immediately before the open chest operation required to graft the harvested vein onto the coronary arteries. The vein harvesting operation is often the most troublesome part of the operation. The long incisions created in the leg can be slow to heal and very painful. Complications resulting from the vein harvesting operation can also hinder the patient's recovery from the entire operation.

Additionally, during the harvesting of the saphenous vein, it is often desirable to leave as much of the pedicle (i.e., between about 4 mm and about 5 mm of perivascular fat surrounding the vein) preserved as possible. The preservation of the pedicle helps the saphenous vein remain uninjured during surgery, and also helps the long-term patency and viability of the saphenous vein. For instance, following the surgery, the pedicle acts as a natural sheath to help prevent the saphenous vein from getting unnaturally distended due to higher arterial pressures.

The method of vein harvesting presented herein is accomplished with endoscopic procedures while preserving much of the pedicle. This allows the vein to be harvested in an operation that requires only a few small incisions, and increases the patency of the vein. Endoscopic surgical techniques for operations such as gall bladder removal and hernia repair are now common. The surgeon performing the operation makes a few small incisions and inserts long tools, including forceps, scissors, and staplers into the incision and deep into the body. Viewing the tools through an endoscope, or a video display from an endoscope, the surgeon can perform all the cutting and suturing operations necessary for a wide variety of operations. The procedures are also referred to as endoscopic surgery, laparoscopic surgery, minimally invasive surgery, or video-assisted surgery. References to endoscopic surgery and endoscopes below is intended to encompass all of these fields, and all operations described below with reference to endoscopes can also be accomplished with laparoscopes, gastroscopes, and any other imaging devices which may be conveniently used.

Minimally invasive procedures for vein removal have been proposed. Knighton, Endoscope and Method for Vein Removal, U.S. Pat. No. 5,373,840 shows a method of cutting the saphenous vein at one end, and grasping the vein with graspers or forceps, then sliding a ring over the vein while securing the vein at the same time. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled in the lumen of the endoscope. As shown in FIGS. 1 and 10 of Knighton, the method requires deployment of the forceps inside the annular dissection loop, and it requires deployment of the loop and graspers inside the endoscope lumen. The blood vessel must be cut and grasped by the forceps before it can be dissected by the dissecting ring.

SUMMARY

The present disclosure relates to a vein harvesting device, comprising a retractor and a drive shaft. The retractor includes an elongated portion defining a longitudinal axis, and supports a first engagement structure including a plurality of first tines. The drive shaft includes an elongated portion, and is movable along the longitudinal axis with respect to the retractor such that the elongated portion of the drive shaft contacts the first engagement structure causing the plurality of first tines to move about the longitudinal axis from a first position to a second position.

In disclosed embodiments, the elongated portion of the retractor supports a second engagement structure including a plurality of second tines. The second engagement structure is movable about the longitudinal axis in response to the drive shaft moving along the longitudinal axis with respect to the retractor. The second engagement structure is movable about the longitudinal axis with respect to the first engagement structure. The first engagement structure is movable in a first direction about the longitudinal axis, the second engagement structure is movable in a second direction about the longitudinal axis, and the first direction is opposite from the second direction. Further, the first engagement structure is movable in the first direction about the longitudinal axis in response to distal movement of the drive shaft with respect to the retractor, and the second engagement structure is movable in the second direction about the longitudinal axis in response to distal movement of the drive shaft with respect to the retractor.

It is further disclosed that the elongated portion of the retractor defines an arcuate channel. Additionally, the elongated portion of the retractor includes an arcuate groove configured for reception of the drive shaft. Further, the elongated portion of the retractor includes an arcuate groove configured for reception of the first engagement structure.

In disclosed embodiments, the elongated portion of the drive shaft defines an arcuate channel.

Additionally, it is disclosed that the elongated portion of the drive shaft includes a member extending along a majority of its length. The member includes a distal camming surface configured to engage the first engagement structure of the retractor. Further, the first engagement structure includes a plurality of first mating members and the second engagement structure includes a plurality of second mating members. Additionally, the plurality of first mating members is movable from a first position wherein the plurality of first mating members contacts the plurality of second mating members, to a second position wherein the plurality of first mating members is spaced from the plurality of second mating members. It is further disclosed that movement of the drive shaft along the longitudinal axis with respect to the retractor causes the plurality of first mating members and the plurality of second mating members to move from the first position to the second position.

It is also disclosed that the plurality of first tines and the plurality of second tines are configured to connect to a source of electrosurgical energy.

The present disclosure also relates to a method of harvesting the saphenous vein and surrounding pedicle. The method includes providing a vein harvesting device comprising a retractor and a drive shaft. The retractor has an elongated portion defining a longitudinal axis, and supports a first engagement structure including a plurality of first tines. The drive shaft includes an elongated portion. The method also includes inserting at least a portion of the retractor adjacent the saphenous vein of a patient, moving the drive shaft along the longitudinal axis with respect to the retractor, contacting the first engagement structure with the drive shaft such that the plurality of first tines moves about the longitudinal axis from a first position to a second position and at least partially encircle at least a portion of the saphenous vein, treating tissue surrounding the pedicle, and removing at least a portion of the saphenous vein and pedicle from the patient.

In disclosed embodiments of the method, the elongated portion of the retractor supports a second engagement structure including a plurality of second tines, and the method further comprises moving the plurality of second tines about the longitudinal axis from a first position to a second position to at least partially encircle at least a portion of the saphenous vein.

It is further disclosed that the method includes inserting at least a portion of the drive shaft through an arcuate groove of the retractor. In disclosed embodiments, treating tissue surrounding the pedicle includes at least one of sealing and cutting tissue, and is performed by a separate surgical instrument.

BRIEF DESCRIPTION OF THE DRAWINGS

Various embodiments of the surgical devices are described herein with reference to the drawings wherein.

DETAILED DESCRIPTION

Figure 1:
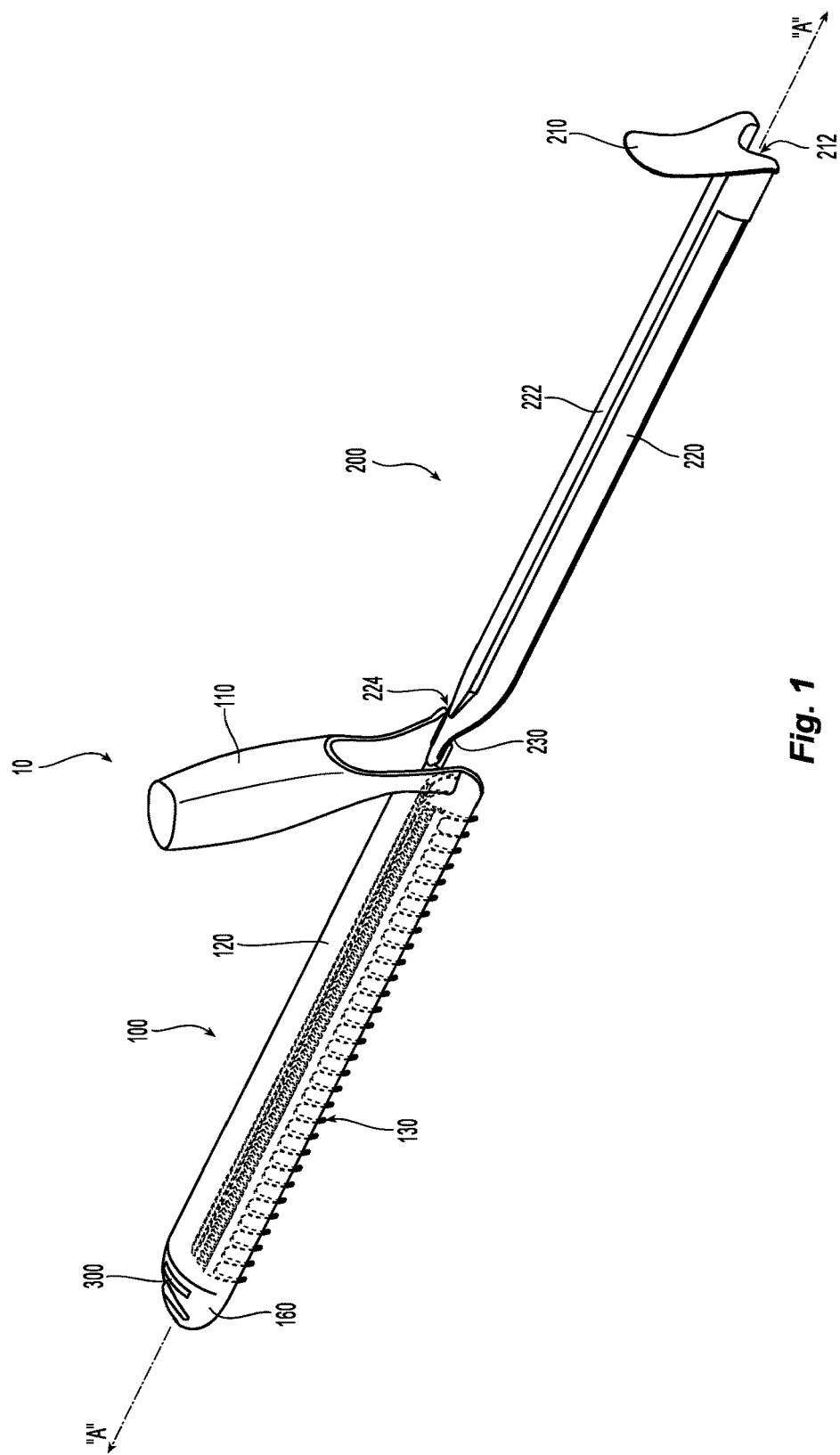
FIG. 1 is a perspective view of a vein harvesting device including a retractor and a drive shaft in accordance with embodiments of the present disclosure.

Embodiments of the presently disclosed vein harvesting device are described in detail with reference to the drawings, in which like reference numerals designate identical or corresponding elements in each of the several views. As used herein the term "distal" refers to that portion of the vein harvesting device that is farther from the user, while the term "proximal" refers to that portion of the vein harvesting device that is closer to the user.

The saphenous vein has a number of tributary veins that carry venous blood into the vein. These tributaries are typically tied off and/or cut off of the saphenous vein before the saphenous vein can be removed. In medical terms, these tributaries must be ligated and divided. When a tributary or side branch is encountered, the surgeon can use endoscopic and laparoscopic tools, for example, to close the tributaries and cut them from the saphenous vein. The tributaries can be separated from the vein after the entire vein is stripped, or the surgeon may choose to separate them as they are encountered.

Referring initially to FIGS. 1-5, one embodiment of a vein harvesting device 10 is shown for use with various surgical procedures and generally includes a retractor 100 and a drive shaft 200. Retractor 100 includes a handle portion 110, an elongated portion 120 defining a longitudinal axis "A-A," and a tip 160. Retractor 100 is configured to releasably engage drive shaft 200. Drive shaft 200 includes a handle portion 210, an elongated portion 220, and a distal portion 230.

Figure 7:
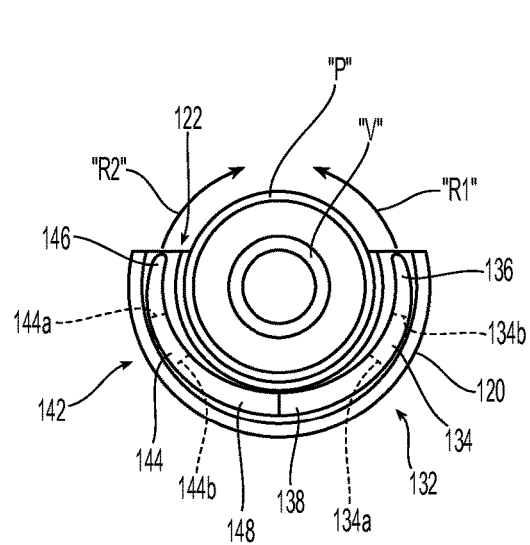
FIG. 7 is a cross-sectional view of the vein harvesting device of FIGS. 1-6 in an open position adjacent a vein.
Figure 8:
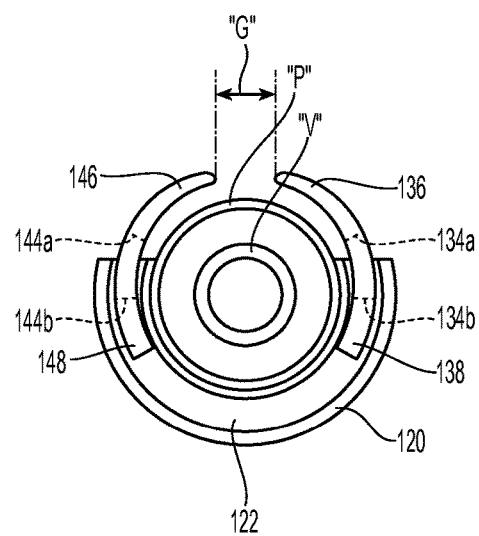
FIG. 8 is a cross-sectional view of the vein harvesting device of FIGS. 1-7 in an approximated position engaging a vein.
Figure 9:
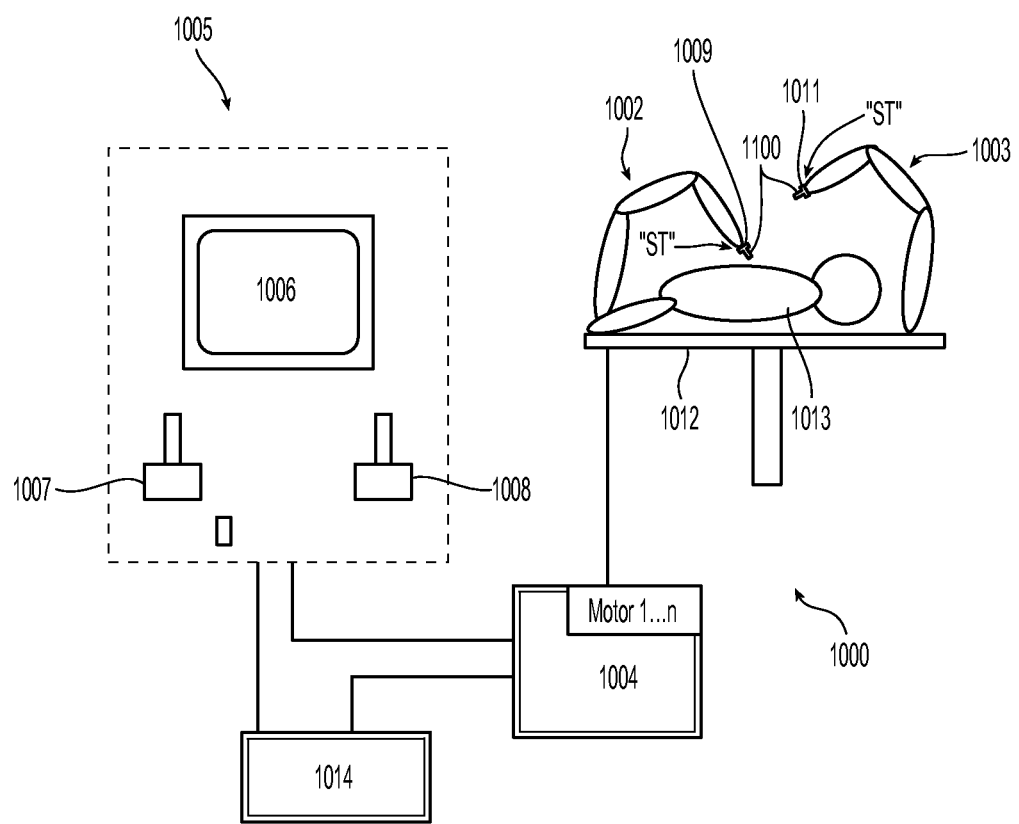
FIG. 9 is a schematic illustration of a surgical system in accordance with the present disclosure.

Vein harvesting device 10 is configured to efficiently remove at least portions of a target vein "V" (e.g., the saphenous vein) while also removing pedicle (i.e., the facial layer surrounding the vein "V") to help the viability of the vein "V" after transplantation thereof (See FIGS. 7 and 8). Additionally, vein harvesting device 10 is configured to be used endoscopically, e.g., to reduce the chances of infection.

Handle portion 110 is disposed at an angle with respect to elongated portion 120, and is configured for grasping by a user. That is, a user can hold handle portion 110 to help insert and/or direct tip 160 and at least part of elongated portion 120 into or within tissue "T."

Elongated portion 120 extends distally from handle portion 110 and includes a plurality of engagement structures 130. The plurality of engagement structures 130 is disposed in a first row of engagement structures 132 and a second row of engagement structures 142. The first row of engagement structures 132 includes a first base 134, a plurality of first tines 136 depending from a first lateral side 134a of first base 134, and a plurality of first mating members 138 depending from a second lateral side 134b of first base 134. The second row of engagement structures 142 includes a second base 144, a plurality of second tines 146 depending from a first lateral side 144a of second base 144, and a plurality of second mating members 148 depending from a second lateral side 144b of second base 144.

Figure 3:
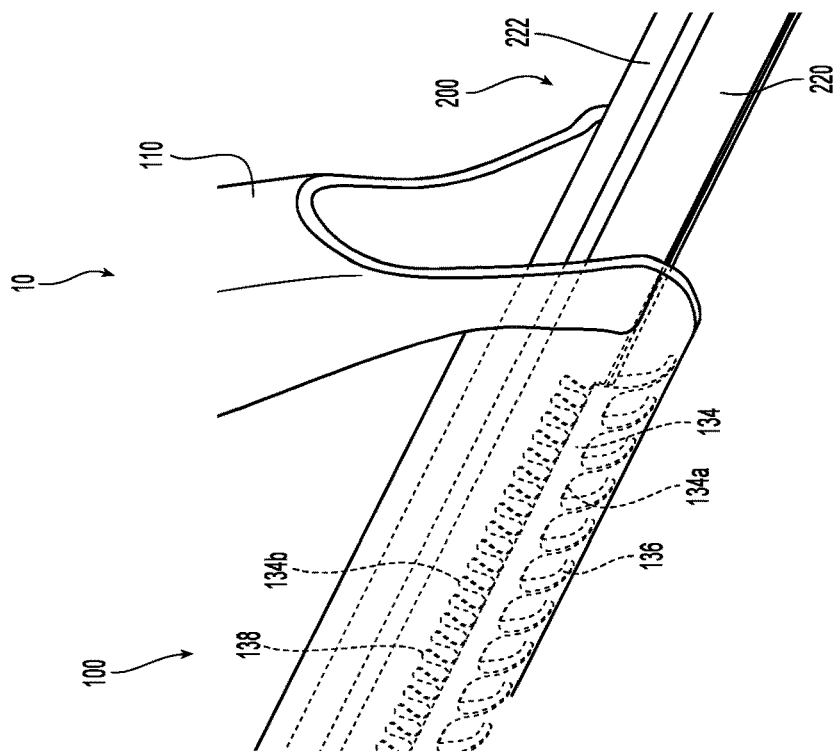
FIG. 3 is a perspective view of a portion of the vein harvesting device of FIGS. 1-2 illustrating the proximal portion of the retractor engaged with a portion of the drive shaft.

As discussed in further detail below, the plurality of first tines 136 and the plurality of second tines 146 are configured to move (e.g., rotate) at least partially about the longitudinal axis "A-A" between a first open position (FIGS. 2 and 7) and a second approximated position (FIGS. 3 and 8), and the plurality of first mating members 138 and the plurality of second mating members 148 are also configured to move (e.g., rotate) at least partially about the longitudinal axis "A-A" between a first engaged position (FIGS. 2 and 7) and a second spaced position (FIGS. 3 and 8).

Figure 5:
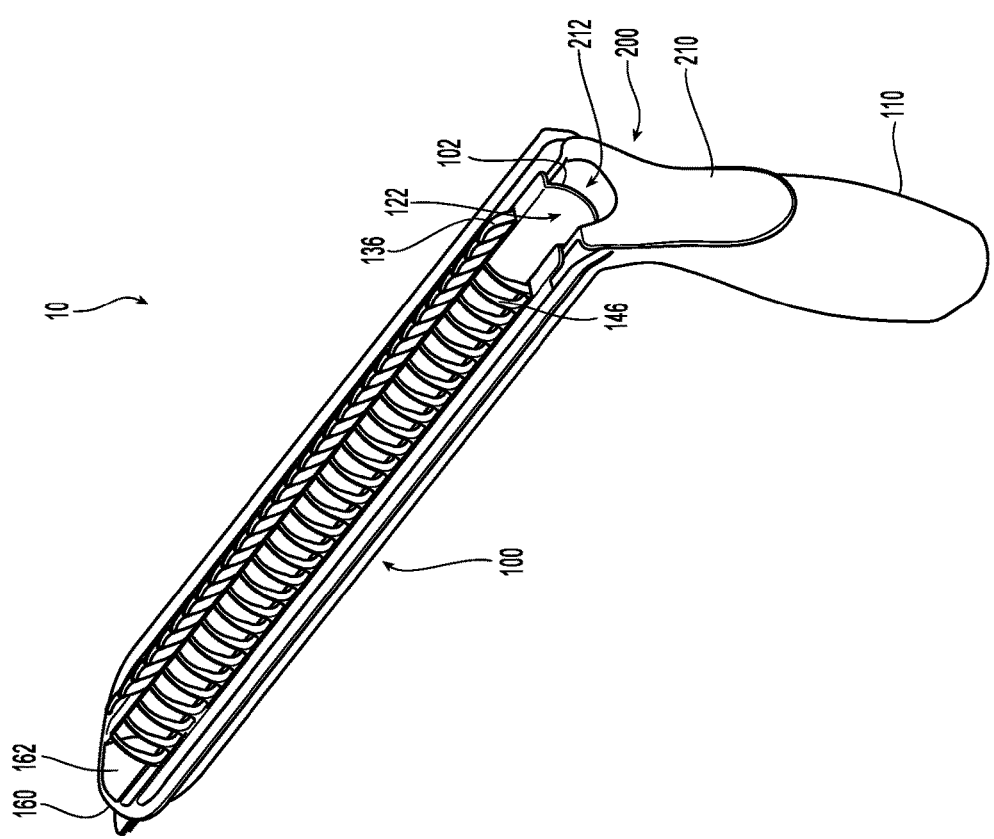
FIG. 5 is a perspective view of the vein harvesting device of FIGS. 1-4 illustrating the retractor engaged with the drive shaft.

A distal portion of retractor 100 includes a blunt tip 160 configured to dissect (e.g., bluntly dissect) or scrape tissue away from the target vein "V" as tip 160 is advanced distally, e.g., while maintaining at least a portion of the pedicle. As shown in FIG. 5, tip 160 is scoop-like in shape, defining a hollow cavity 162 therein. The scoop-like shape of tip 160 is configured to scrape tissue away from the target vein "V." Additionally, at least a portion of retractor 100 (e.g., the entirety of tip 160) may be transparent or translucent. The transparency or translucency of tip 160 facilitates the viewing of target tissue and the vein "V" by a surgeon or an endoscope, and allows light to shine through tip 160 to illuminate the target tissue and the vein "V."

With regard to drive shaft 200, handle portion 210 is disposed at an angle with respect to elongated portion 220, and is configured for grasping by a user. That is, a user can hold handle portion 210 to help insert and/or direct distal portion 230 and at least part of elongated portion 220 into or within retractor 100.

Elongated portion 220 extends distally from handle portion 210 and distally terminates in distal portion 230. Elongated portion 220 includes a member 222 thereon. Member 222 extends along a majority of elongated portion 220 and includes distal camming surfaces 224. Distal camming surfaces 224 are configured to engage first base 134 and second base 144, as discussed in further detail below. Distal portion 230 of elongated portion 220 includes a blunt tip 232 configured to extend between first base 134 and second base 144.

Figure 2:
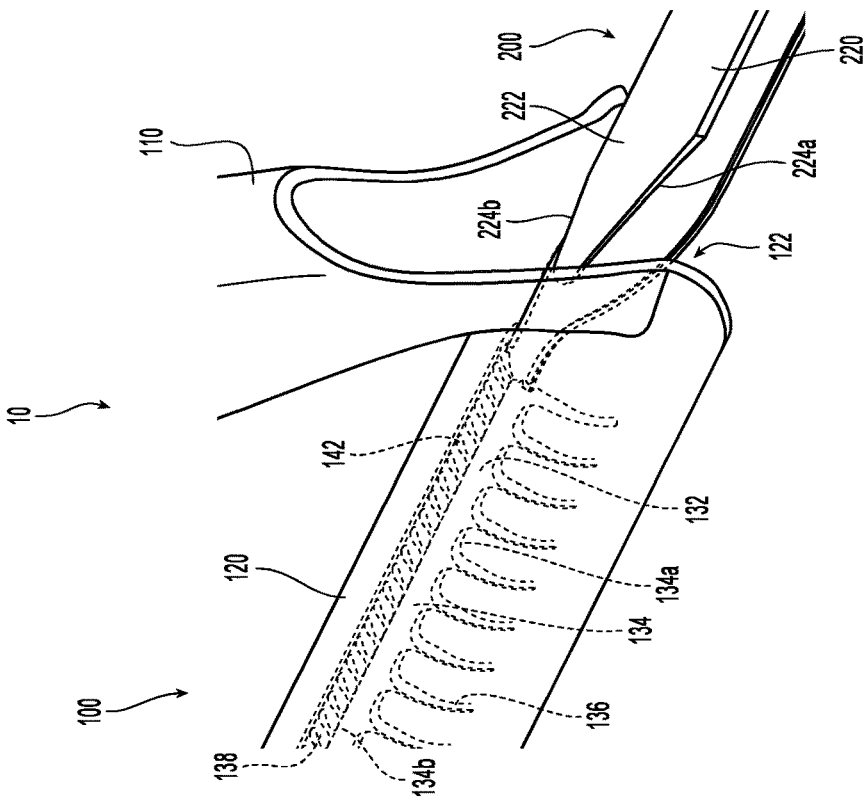
FIG. 2 is a perspective view of a portion of the vein harvesting device of FIG. 1 illustrating a proximal portion of the retractor prior to engagement with a distal portion of the drive shaft.

In use, tip 160 and at least a portion of elongated portion 120 of retractor 100 are inserted through an incision "I" in a patient. In particular, retractor 100 is inserted through the incision "I" when plurality of first tines 136 and plurality of second tines 146 are in their first open position, and correspondingly, when plurality of first mating members 138 and plurality of second mating members 148 are in their first engaged position (FIGS. 2 and 7). Further, an arcuate channel 122 of elongated portion 120 is positioned adjacent (e.g., in contact with) pedicle "P" surrounding a vein "V" (e.g., the saphenous vein) (FIG. 7).

Next, distal portion 230 of drive shaft 200 is inserted through and/or within arcuate channel 122 of elongated portion 120 of retractor 100 such that distal portion 230 is positioned between first base 134 and second base 144. Drive shaft 200 also includes an arcuate channel 212 that is configured to essentially match the curvature of arcuate channel 122 of elongated portion 120, and to substantially match the curvature of a patient's pedicle "P" or vein "V," for instance. The radius of curvature of arcuate channel 122 of elongated portion 120 of retractor 100 and the radius of curvature of arcuate channel 212 of drive shaft 200 may be between about 3 mm and about 10 mm.

Figure 4:
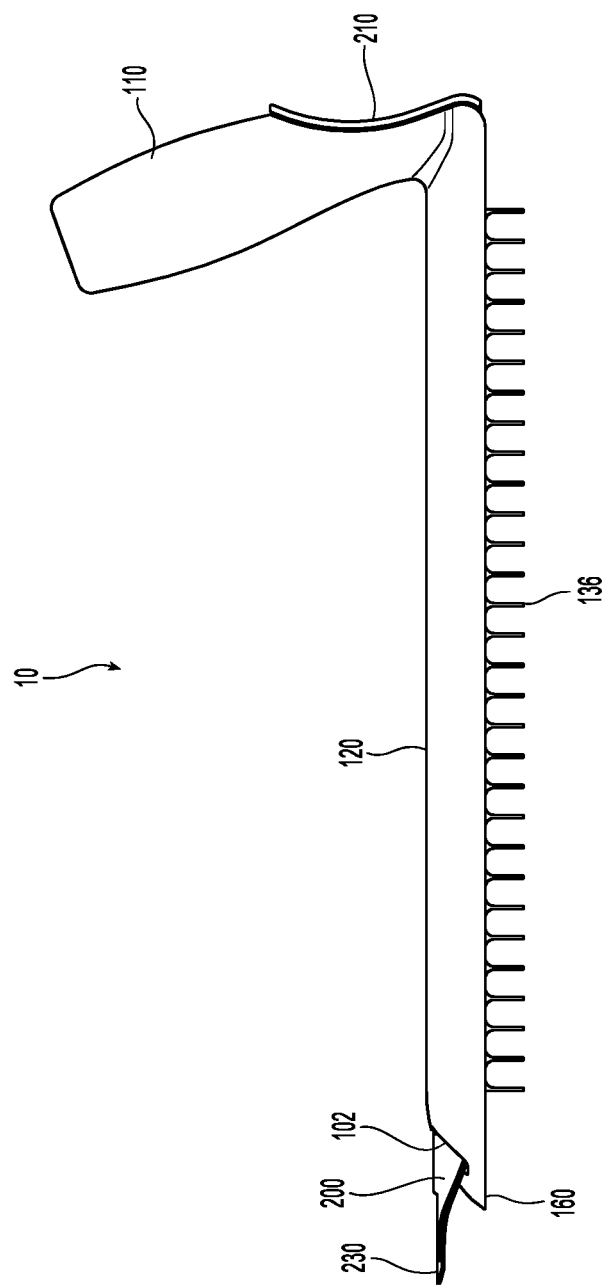
FIG. 4 is a side view of the vein harvesting device of FIGS. 1-3 illustrating the retractor engaged with the drive shaft.

As shown in FIG. 5, retractor 100 includes an elongated, arcuate groove 102 configured for reception of elongated portion 220 of drive shaft 200, for example. First row of engagement structures 132 and second row of engagement structures 142 may also be rotatably supported within elongated, arcuate groove 102. A distal end of arcuate groove 102 is shown in FIG. 4.

Continued distal advancement of drive shaft 200 causes distal camming surfaces 224 of member 222 to contact first row of engagement structures 132 and second row of engagement structures 142 of elongated portion 120, which causes plurality of first tines 136 and plurality of second tines 146 to move from their first open position toward their second approximated position, and which causes plurality of first mating members 138 and plurality of second mating members 148 to move from their first engaged position toward their second spaced position (FIG. 8).

More particularly, distal advancement of drive shaft 200 with respect to retractor 100 causes a first distal camming surface 224a of member 222 to contact first row of engagement structures 132 (e.g., a camming surface thereon), and causes a second distal camming surface 224b of member 222 to contact second row of engagement structures 142 (e.g., a camming surface thereon) (see FIG. 2). The engagement between first distal camming surface 224a and first row of engagement structures 132 causes first row of engagement structures 132 to rotate about the longitudinal axis "A-A" in a first direction as indicated by arrow "R1" in FIG. 7, such that plurality of first tines 136 at least partially surround the patient's pedicle "P" and vein "V" (FIG. 8). The engagement between second distal camming surface 224b and second row of engagement structures 142 causes second row of engagement structures 142 to rotate about the longitudinal axis "A-A" in a second direction as indicated by arrow "R2" in FIG. 7, such that plurality of second tines 146 at least partially surround the patient's pedicle "P" and vein "V" (FIG. 8).

Additionally, since plurality of first mating members 138 is part of first row of engagement structures 132 and since plurality of second mating members 148 is part of second row of engagement structures 142, the rotation of first row of engagement structures 132 and second row of engagement structures 142 about the longitudinal axis "A-A" also causes the rotation of plurality of first mating members 138 and plurality of second mating members 148 about the longitudinal axis "A-A."

Complete distal advancement of drive shaft 200 with respect to retractor 100 causes all first tines of plurality of first tines 136 and all second tines of plurality of second tines 146 to move into their second, approximated positions. As shown in FIG. 8, movement of plurality of first tines 136 and plurality of second tines 146 toward their second approximated position results in plurality of first tines 136 and plurality of second tines 146 at least partially surrounding the patient's pedicle "P" and vein "V."

Further, the particular sizes of plurality of first tines 136 and plurality of second tines 146 helps dictate the size of the gap "G," if any, exists between plurality of first tines 136 and plurality of second tines 146 when disposed in their second, approximated position (FIG. 8). The plurality of first tines 136 and plurality of second tines 146 may include any suitable size to create a desired gap "G" size (including no gap "G"). The drive shaft 200 and retractor 100 can lockingly engage one other with suitable mechanical structure, such as upon complete distal advancement of drive shaft 200 with respect to retractor 100.

To move plurality of first tines 136 and plurality of second tines 146 back to their first, open positions, and to move plurality of first mating members 138 and plurality of second mating members 148 back to their first, engaged position, drive shaft 200 is moved proximally with respect to retractor 100. The plurality of first tines 136, plurality of second tines 146, plurality of first mating members 138, and plurality of second mating members 148 may be biased toward their first positions.

When first tines of plurality of first tines 136 and second tines of plurality of second tines 146 are in their second, approximated positions at least partially surrounding the patient's pedicle "P" and vein "V," the pedicle "P" and vein "V" are physically protected by vein harvesting device 10, for example from other instruments. Additionally, the vein "V" and surrounding pedicle "P" can together be removed from the patient (e.g., after separation from bodily tissue) by moving vein harvesting device 10 proximally with respect to the patient, e.g., while plurality of first tines 136 and plurality of second tines 146 are in their second, approximated positions. The removal of the vein "V" along with the pedicle "P" helps reduce undue stress on the vein "V," and helps ensure the long-term patency of the final graft.

Figure 6:
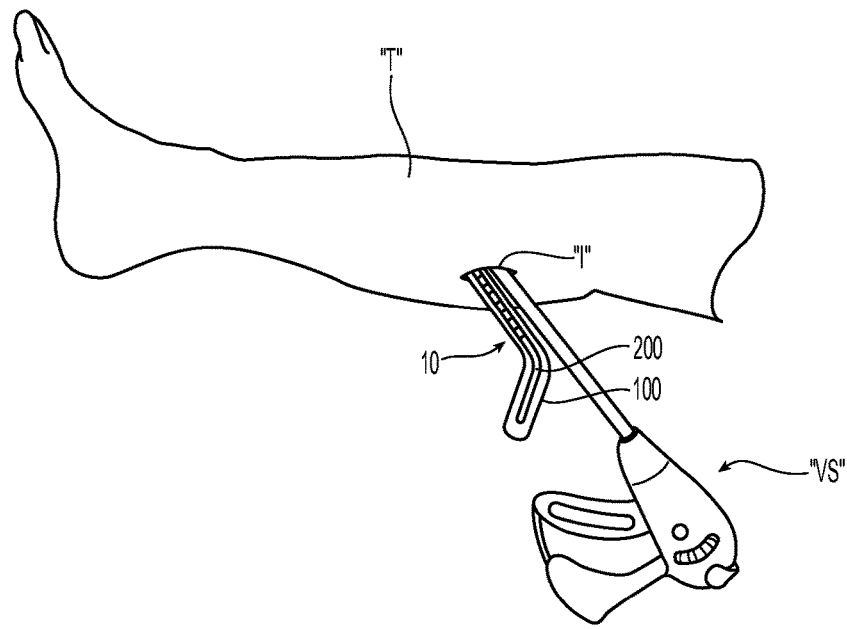
FIG. 6 illustrates the vein harvesting device of FIGS. 1-5 with its distal end within a patient, and another surgical instrument with its distal end within the patient, in accordance with embodiments of the present disclosure.

To help separate the patient's pedicle "P" and vein "V" from surrounding tissue, it is envisioned that a vessel sealing device "VS" (FIG. 6) can be used. For instance, a vessel sealing device "VS" can be inserted through incision "I" (or a separative incision) such that its end effector is adjacent the pedicle "P." A user can then cut and/or seal side branches of the vein "V" with the end effector to allow the vein "V" to be removed from the patient. Details of a vessel sealing device including a handle assembly for controlling actuation of an end effector can be found in U.S. patent application Ser. Nos. 10/179,863 and 10/116,944, the entire contents of which being incorporated by reference.

Plurality of first tines 136 and plurality of second tines 146 of retractor 100 may be made of metal or include a metalized component to enable retractor 100 to provide bipolar RF heating of the tissue when plurality of first tines 136 and plurality of second tines 146 are in their second, approximated position. Here, plurality of first tines 136 has a first polarity and plurality of second tines 146 has a second polarity, for example. In such embodiments, vein harvesting device 10 has the ability to seal or fuse tissue (e.g., side branches), which can eliminate the need for a separate surgical instrument (e.g., a vessel sealing device "VS") to be used to seal or fuse tissue. Here, retractor 100 is configured for connection to electrosurgical energy.

With reference to FIG. 1, another feature of vein harvesting device 10 is shown according to embodiments of the present disclosure. Here, vein harvesting device 10 includes an ultrasound probe 300. In the illustrated embodiments, ultrasound probe 300 is disposed adjacent tip 160 of retractor 100, but other locations for placement of ultrasound probe may be utilized. The inclusion of ultrasound probe 300 enables a surgeon to determine the exact location of the particular portion of vein harvesting device 10 with respect to the target vein "V." Traditional endoscopic vein harvesting systems rely on direct visualization of the skeletonized vein by means of an endoscopic camera, for example. However, relying on an endoscopic camera to harvest the vein inclusive of the pedicle is difficult because the vein "V" is often hidden inside the fascia.

The present disclosure also includes methods of performing vein harvesting operations using vein harvesting device 10 discussed herein, and methods of manufacturing vein harvesting device 10 discussed herein.

Methods and devices presented herein take advantage of laparoscopic procedures to lessen the trauma of vein harvesting operations. Instead of making an incision along or over the entire length, or essentially the entire length of the vein "V" to be harvested, the procedure may be conducted with only a few small incisions or a single incision. All that is needed is a working space large enough to allow the surgeon to use vein harvesting device 10 and view the operation through a laparoscope, for example. In disclosed embodiments of the method, the surgeon creates a working space under the skin and over the saphenous vein using laparoscopic techniques. The surgeon makes one or several small incisions to expose the saphenous vein. These incisions are referred to as cut-downs. A distal incision near the knee and/or a proximal incision at the groin may be used. If the entire length of the saphenous vein is to be harvested, an additional incision can be made close to the ankle. The saphenous vein can be seen through the cut-downs. The use of three or four incisions used to harvest the entire saphenous vein are merely a matter of convenience, and those particularly skilled in laparoscopic procedures may require fewer incisions, and also more small incisions may be desired.

After the incision(s), the surgeon inserts vein harvesting device 10 into one incision and pushes it along the saphenous vein "V" towards the other incision. The tunneling creates a channel running along the saphenous vein "V." The channel may be expanded by insertion of a balloon (not shown), which can be inflated to expand or propagate the tunnel further along the saphenous vein "V".

A balloon (not shown) may packed inside vein harvesting device 10. The balloon is a non-elastomeric balloon or bladder and may be deployed through a balloon trocar extending along at least a portion of the length of vein harvesting device 10. When used for tunneling along the saphenous vein "V," the balloon may be approximately 60 centimeters long, and the balloon trocar may be between about 10 centimeters to about 20 centimeters long. Injecting liquid or gas into the balloon through an inflation port expands the balloon. Sterile saline solution is an example of an inflation medium for medical applications. Alternately, air, $CO_2$, or even foam or other substances may be injected to cause inflation. Further details of the balloon and its use for harvesting veins are disclosed in U.S. patent application Ser. No. 12/550,462, the entire contents of which being incorporated by reference herein.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

With particular reference to FIG. 7, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical instrument 10 (including end effector 300) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A vein harvesting device, comprising:
a retractor including an elongated portion defining a longitudinal axis, the elongated portion supporting a first engagement structure including a plurality of first tines and a second engagement structure including a second plurality of tines; and
a drive shaft including an elongated portion, the drive shaft movable along the longitudinal axis with respect to the retractor such that the elongated portion of the drive shaft contacts the first engagement structure causing the plurality of first tines and the plurality of second tines to rotate about the longitudinal axis from a first position to a second position.

2. The vein harvesting device according to claim 1, wherein the second engagement structure is movable about the longitudinal axis with respect to the first engagement structure.

3. The vein harvesting device according to claim 1, wherein the first engagement structure is movable in a first direction about the longitudinal axis, the second engagement structure is movable in a second direction about the longitudinal axis, and wherein the first direction is opposite from the second direction.

4. The vein harvesting device according to claim 3, wherein the first engagement structure is movable in the first direction about the longitudinal axis in response to distal movement of the drive shaft with respect to the retractor, and wherein the second engagement structure is movable in the second direction about the longitudinal axis in response to distal movement of the drive shaft with respect to the retractor.

5. The vein harvesting device according to claim 1, wherein the elongated portion of the retractor defines an arcuate channel.

6. The vein harvesting device according to claim 5, wherein the elongated portion of the retractor includes an arcuate groove configured for reception of the drive shaft.

7. The vein harvesting device according to claim 5, wherein the elongated portion of the retractor includes an arcuate groove configured for reception of the first engagement structure.

8. The vein harvesting device according to claim 1, where the elongated portion of the drive shaft defines an arcuate channel.

9. The vein harvesting device according to claim 1, wherein the elongated portion of the drive shaft includes a member extending along a majority of a length thereof, the member includes a distal camming surface configured to engage the first engagement structure of the retractor.

10. The vein harvesting device according to claim 1, wherein the first engagement structure includes a plurality of first mating members and wherein the second engagement structure includes a plurality of second mating members.

11. The vein harvesting device according to claim 10, wherein the plurality of first mating members is movable from a first position wherein the plurality of first mating members contacts the plurality of second mating members, to a second position wherein the plurality of first mating members is spaced from the plurality of second mating members.

12. The vein harvesting device according to claim 11, wherein movement of the drive shaft along the longitudinal axis with respect to the retractor causes the plurality of first mating members and the plurality of second mating members to move from the first position to the second position.

13. The vein harvesting device according to claim 1, wherein the plurality of first tines and the plurality of second tines are configured to connect to a source of electrosurgical energy.

14. The vein harvesting device according to claim 1, wherein at least one tine of the plurality of first tines includes a concave portion, and wherein the concave portion of the at least one tine faces the longitudinal axis when the plurality of first tines is in the second position.

15. A vein harvesting device, comprising:
a retractor including an elongated portion defining a longitudinal axis, the elongated portion supporting a first engagement structure including a plurality of first tines; and
a drive shaft including an elongated portion, the drive shaft movable along the longitudinal axis with respect to the retractor such that the elongated portion of the drive shaft contacts the first engagement structure causing the plurality of first tines to move about the longitudinal axis from a first position to a second position, the elongated portion of the drive shaft defining an arcuate channel.

16. The vein harvesting device according to claim 15, wherein the elongated portion of the retractor supports a second engagement structure including a plurality of second tines.

17. The vein harvesting device according to claim 16, wherein the plurality of first tines and the plurality of second tines are configured to rotate about the longitudinal axis.

18. The vein harvesting device according to claim 16, wherein the plurality of first tines and the plurality of second tines are configured to connect to a source of electrosurgical energy.

19. The vein harvesting device according to claim 15, wherein the elongated portion of the retractor defines an arcuate channel.

20. The vein harvesting device according to claim 15, wherein the elongated portion of the drive shaft includes a member extending along a majority of a length thereof, the member includes a distal camming surface configured to engage the first engagement structure of the retractor.

* * * * *